(12) United States Patent
Wood et al.

(10) Patent No.: US 8,884,001 B2
(45) Date of Patent: Nov. 11, 2014

(54) PREPARATION OF INTERMEDIATES USEFUL IN THE SYNTHESIS OF 2'-CYANO-2'-DEOXY-N4-PALMI-TOYL-1-β-D-ARABINOFURANOSYLCYTOSINE

(75) Inventors: Gavin Wood, Cupar Fife (GB); Robert Westwood, Oxon (GB); Tsuyoshi Murofushi, Hiratsuka (JP); Eiji Numagami, Fujisawa (JP); Takashi Takita, Hiratsuka (JP)

(73) Assignee: Cyclacel Limited, London (GB)

( * ) Notice: Subject to any disclaimer, the term of this patent is extended or adjusted under 35 U.S.C. 154(b) by 613 days.

(21) Appl. No.: 12/991,582

(22) PCT Filed: May 8, 2009

(86) PCT No.: PCT/GB2009/001134
§ 371 (c)(1),
(2), (4) Date: Apr. 29, 2011

(87) PCT Pub. No.: WO2009/136158
PCT Pub. Date: Nov. 12, 2009

(65) Prior Publication Data
US 2011/0224421 A1    Sep. 15, 2011

(30) Foreign Application Priority Data

May 8, 2008    (GB) .................................. 0808357.8

(51) Int. Cl.
*C07H 19/06*    (2006.01)
*C07F 7/08*    (2006.01)
(52) U.S. Cl.
CPC .................................. *C07F 7/0841* (2013.01)
USPC ........................ 536/28.2; 536/28.5; 536/28.51
(58) Field of Classification Search
USPC ........................ 536/28.2, 28.5, 28.51
See application file for complete search history.

(56) References Cited

U.S. PATENT DOCUMENTS 4,086,417 A * 4/1978 Ishida et al. ................ 536/26.21
5,691,319 A * 11/1997 Kaneko et al. .................. 514/49
(Continued)

FOREIGN PATENT DOCUMENTS

EP      0536936 A1 * 4/1993 ........... C07H 19/073
JP      7-53586      2/1995
(Continued)

OTHER PUBLICATIONS

Oba et al, Tetrahedron Letters, 2003, 44, 4027-29.*

(Continued)

*Primary Examiner* — Ganapathy Krishnan
(74) *Attorney, Agent, or Firm* — Nelson Mullins Riley & Scarborough LLP; Jane E. Remillard, Esq.; Cynthia L. Kanik

(57) ABSTRACT

The present invention relates to a process for preparing a compound of formula 682-4, said process comprising the steps of: (i) converting a compound of formula 682-1 into a compound of formula 682-2; (ii) converting said compound of formula 682-2' into a compound of formula 682-3; and (iii) converting said compound of formula 682-3 into a compound of formula 682-4. Further aspects of the invention relate to the use of the above process in the preparation of 2'-cyano-2'-deoxy-$N^4$-palmitoyl-1-β-D-arabmofuranosylcytosine, a pyrimidine nucleoside which is therapeutically useful in the treatment and/or prevention of cancer.

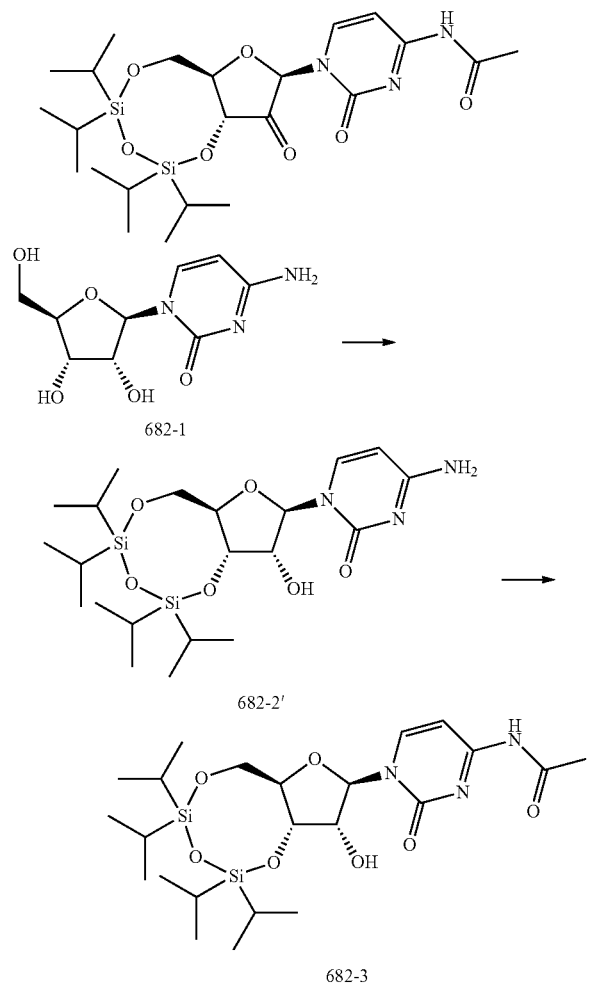

17 Claims, 2 Drawing Sheets

(56) References Cited

U.S. PATENT DOCUMENTS 6,531,584 B1    3/2003   Cook et al.
6,908,906 B2 *  6/2005   Takita et al. ............... 514/49

FOREIGN PATENT DOCUMENTS

| JP | 07053586 | * | 2/1995 | ............ C07H 19/06 |
| WO | 02/064609 A1 | | 8/2002 | |
| WO | 2007/072061 A2 | | 6/2007 | |

OTHER PUBLICATIONS

Greene et al, Protective Groups in Organic Synthesis, 2nd Ed., 1991, pp. 74-75, 349-350.*

Markiewicz, Wojciech T. et al., "The Reaction of 1,3-Dichloro-1,1,3,3-Tetraisopropyl-Disiloxane with Cytosine Arabinoside and 1-(6-Deoxy-alpha-L-Talofuranosyl)Uracil," Collection Czechoslov. Chem. Commun., vol. 45:1860-1865 (1980).

Schwans, Jason P. et al., "A Packing-Density Metric for Exploring the Interior of Folded RNA Molecules," Angew. Chem. Int. Ed., vol. 43:3033-3037 (2004).

International Preliminary Report on Patentability for Application No. PCT/GB2009/001134, dated Nov. 9, 2010, pp. 1-8.

Aoshima, Michiko et al., "Antitumor Activities of Newly Synthesized N4-Acyl-1-beta-D-arabinofuranosylcytosine," Cancer Research, vol. 36:2726-2732 (1976).

Appell, Robert B. et al., "New Synthesis of a Protected Ketonucleoside by a Non-Cryogenic Oxidation wtih TFAA/DMSO," Organic Process Research & Development, vol. 4:172-174 (2000).

Buff, Rolf et al., "2'-Ethynyl-DNA: Synthesis and Pairing Properties," Helvetica Chimica Acta, vol. 85:224-254 (2002).

Burch, P.A. et al., "Phase I Study of Orally Administered CS-682 in Solid Tumors," Proceedings of ASCO, vol. 20:92a, Poster Presentation No. 364, 1 page (2001).

Chatgilialoglu, C. et al., "Tris(trimethylsily)silane. A New Reducing Agent," J. Org. Chem., vol. 53:3641-3642 (1988).

Clark, Jeremy L. et al., "Design, Synthesis, and Antiviral Activity of 2'-Deoxy-2'fluoro-2'-C-methylcytidine, a Potent Inhibitor of Hepatitis C Virus Replication," J. Med. Chem., vol. 48:5504-5508 (2005).

Cook, A.F. et al., "Fluorinated Pyrimidine Nucleosides. 3. Synthesis and Antitumor Activity of a Series of 5'-Deoxy-5-fluoropyrimidine Nucleosides," Journal of Medicinal Chemistry, vol. 22(11):1330-1335 (1979).

Donehower, Ross et al., "A Phase I Study of CS-682, an Oral Antimetabolite, in Patients with Refractory Solid Tumors," ASCO, American Society of Clinical Oncology Annual Meeting, Proc. Am. Soc. Clin. Oncol., vol. 19, Abstract No. 764, 2 pages (2000).

Duschinsky, Robert et al., "The Synthesis of 5-Fluoropyrimidines," J. Am. Chem. Soc., vol. 79:4559-7560 (1957).

Evans, John S. et al., "Antitumor Activity of 1-beta-D-Arabinofuranosylcytosine Hydrochloride," Proc. Soc. Exp. Bio. Med., vol. 106:350-353 (1961).

Fujii, Setsuro et al., "Effect of Uracil and its Derivatives of Antitumor Activity of 5-Fluorouracil and 1-(2-Tetrahydrofuryl)-5-Fluorouracil," Gann, vol. 69:763-772 (1978).

Giller, S.A. et al., "Analogs of pyrimidine nucleosides," Dokl. Akad. Nauk SSSR, vol. 176(2):332-335 (1967).

Hanaoka, Kenji et al., "Antitumor Activity and Novel DNA-Self-Strand-Breaking Mechanism of CNDAC (1-(2-Cyano-2-Deoxy-beta-D-Arabino-Pentofuranosyl) Cytosine) and its N4-Palmitoyl Derivatives (CS-682)," Int. J. Cancer, vol. 82:226-236 (1999).

Holde, D. et al., "Anhydrides of palmitic and stearic acids," Ber Deut Chem Gesellschaft, vol. 57B:103-104 (1924).

Hoshi, Akio et al., "Antitumor Activity of Cyclocytidine in a Variety of Tumors," Gann, vol. 63:353-360 (1972).

Hoshi, Akio et al., "Antitumor Activity of 1-Hexylcarbamoyl-5-Fluorouracil in a Variety of Experimental Tumors," Gann, vol. 67:725-731 (1976).

Oba, Makoto et al., "Radical-based transformation of vicinal diols of olefins via thioxocarbamate derivatives: a simple approach to 2',3'-didehydro-2',3'-dideoxynucleosides," Tetrahedron Letters, vol. 44:4027-4029 (2003).

Samano, Vicente et al., "Mild Periodinane Oxidation of Protected Nucleosides to Give 2'- and 3'-Ketonucleosides. The First Isolation of a Purine 2'-Deoxy-3'-ketonucleoside Derivative," J. Org. Chem., vol. 55:5186-5188 (1990).

Shing, Tony K.M. et al., "A synthetic approach toward taxol analogs: studies on the construction of the CD ring," Tetrahedron, vol. 60:9179-9197 (2004).

Wu, Ming et al., "High-resolution Magnetic Resonance Imaging of the Efficacy of the Cytosine Analogue 1-[2-C-Cyano-2-deoxy-beta-D-arabino-pentofuranosyl]-N4-palmitoyl Cytosine (CS-682) in a Liver-Metastasis Athymic Nude Mouse Model," Cancer Research, vol. 63:2477-2482 (2003).

Zhong, Minghong et al., "Synthesis of the Ribosomal P-Site Substrate CCA-pcb," Organic Letters, vol. 8(1):55-58 (2006).

* cited by examiner

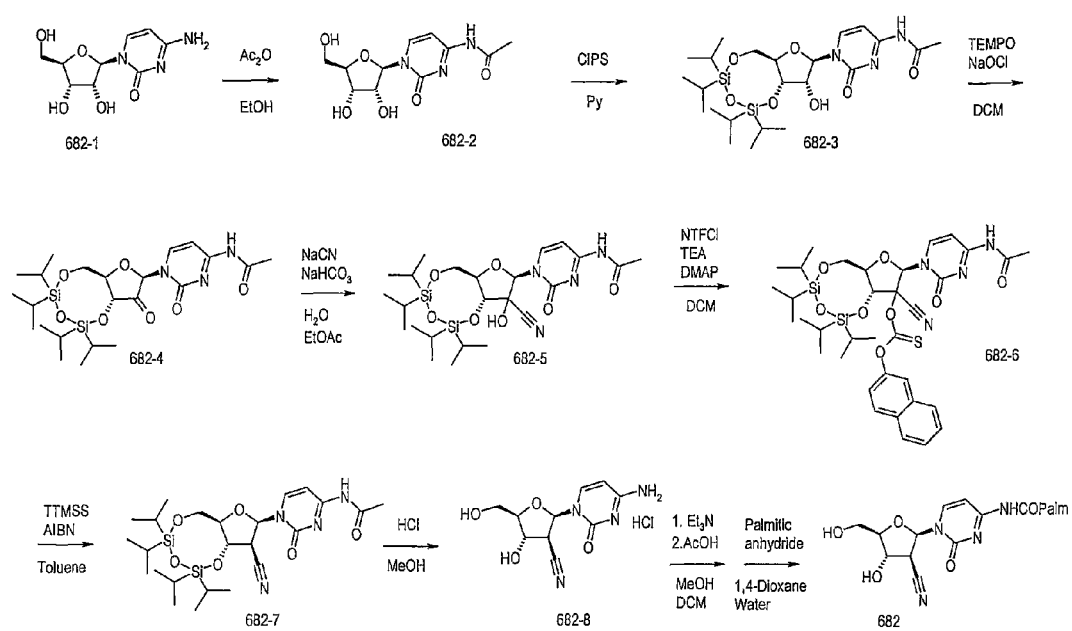
FIGURE 1 (ROUTE 1)

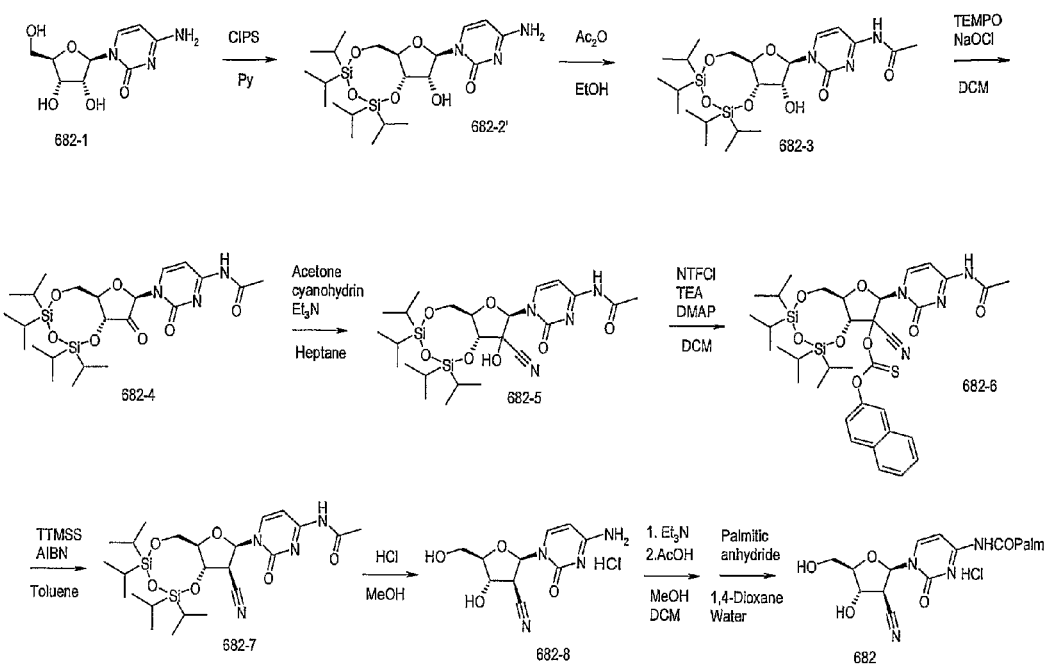
FIGURE 2 (ROUTE 1A)

PREPARATION OF INTERMEDIATES USEFUL IN THE SYNTHESIS OF 2'-CYANO-2'-DEOXY-N4-PALMI-TOYL-1-β-D-ARABINOFURANOSYLCYTOSINE

This application is a 35 U.S.C. §371 filing of International Application Number PCT/GB2009/001134 which was filed on May 8, 2009, which claims priority to Great Britain Application 0808357.8, which was filed on May 8, 2008. The entire contents of the aforementioned applications are hereby incorporated herein by reference. The contents of any patents, patent applications, and references cited throughout this specification are hereby incorporated by reference in their entireties.

The present invention relates to the preparation of intermediates useful in the synthesis of 2'-cyano-2'-deoxy-$N^4$-palmitoyl-1-β-D-arabinofuranosylcytosine, a pyrimidine nucleoside therapeutically useful in the treatment and/or prevention of cancer. Specifically, the invention provides an improved process for the preparation of 2'-cyano-2'-deoxy-$N^4$-palmitoyl-1-O-D-arabinofuranosylcytosine.

BACKGROUND TO THE INVENTION

The therapeutic use of pyrimidine nucleosides in the treatment of proliferative disorders has been well documented in the art. By way of example, commercially available antitumor agents of the pyrimidine series include 5-fluorouracil (Duschinsky, R., et al., J. Am. Chem. Soc., 79, 4559 (1957)), Tegafur (Hiller, S A., et al., Dokl. Akad. Nauk USSR, 176, 332 (1967)), UFT (Fujii, S., et al., Gann, 69, 763 (1978)), Carmofur (Hoshi, A., et al., Gann, 67, 725 (1976)), Doxyfluridine (Cook, A. F., et al., J. Med. Chem., 22, 1330 (1979)), Cytarabine (Evance, J. S., et al., Proc. Soc. Exp. Bio. Med., 106. 350 (1961)), Ancytabine (Hoshi, A., et al., Gann, 63, 353, (1972)) and Enocytabine (Aoshima, M., et al., Cancer Res., 36, 2726 (1976)).

EP 536936 (Sankyo Company Limited) discloses various 2'-cyano-2'-deoxy-derivatives of 1-β-D-arabinofuranosylcytosine which have been shown to exhibit valuable anti-tumour activity. One particular compound disclosed in EP 536936 is 2'-cyano-2'-deoxy-$N^4$-palmitoyl-1-β-D-arabinofuranosylcytosine (referred to hereinafter as "682" or "CYC682"); this compound is currently under further investigation.

CYC682, also known as 1-(2-C-cyano-2-dioxy-(3-D-arabino-pentofuranosyl)-$N^4$-palmitoyl cytosine, (Hanaoka, K., et al, Int. J. Cancer, 1999:82:226-236; Donehower R, et al, Proc Am Soc Clin Oncol, 2000: abstract 764; Burch, P A, et al, Proc Am Soc Clin Oncol, 2001: abstract 364), is an orally administered novel 2'-deoxycytidine antimetabolite prodrug of the nucleoside CNDAC, 1-(2-C-Cyano-2-deoxy-β-D-arabino-pentafuranosyl)-cytosine.

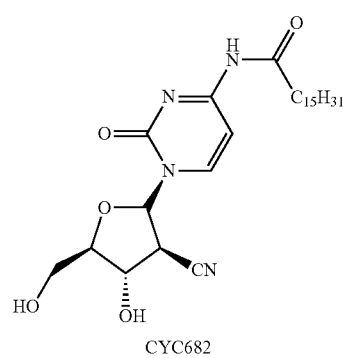

CYC682

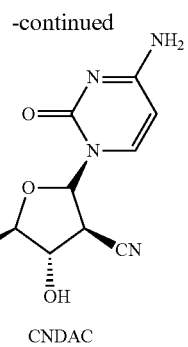

CNDAC

CYC682 has a unique mode of action over other nucleoside metabolites such as gemcitabine in that it has a spontaneous DNA strand breaking action, resulting in potent anti-tumour activity in a variety of cell lines, xenograft and metastatic cancer model.

CYC682 has been the focus of a number of studies in view of its oral bioavailability and its improved activity over gemcitabine (the leading marketed nucleoside analogue) and 5-FU (a widely-used antimetabolite drug) based on preclinical data in solid tumours. Recently, investigators reported that CYC682 exhibited strong anticancer activity in a model of colon cancer. In the same model, CYC682 was found to be superior to either gemcitabine or 5-FU in terms of increasing survival and also preventing the spread of colon cancer metastases to the liver (Wu M, et al, Cancer Research, 2003: 63:2477-2482). To date, phase I data from patients with a variety of cancers suggest that CYC682 is well tolerated in humans, with myelosuppression as the dose limiting toxicity.

More recent studies have focussed on different crystalline forms of CYC682 (see for example, WO 02/064609 in the name of Sankyo Company Limited) and optimised formulations containing CYC682 which exhibit improved stability and which allow easier processing (see for example, WO 07/072,061 in the name of Cyclacel Limited).

The preparation of CYC682 described in EP 536936 (see Scheme 1 below) involves reacting cytidine [1] with palmitic anhydride in DMF to form $N^4$-palmitoylcytidine [2] and subsequently protecting with 1,3-dichloro-1,1,4,4-tetraisopropyldisiloxane (CIPS) to form intermediate [3]. Oxidation of [3] with pyridinium dichromate/acetic anhydride in dichloromethane produces intermediate ketone [4], which is then reacted with sodium cyanide and sodium dihydrogen phosphate dihydrate in ethyl acetate to form the cyanohydrin [5]. Intermediate [5] is then reacted with N,N-dimethylaminopyridine, phenoxythiocarbonyl chloride and triethylamine to form intermediate [6], which is subsequently reacted with AIBN and tributyltin hydride in toluene to give intermediate [7]. Deprotection of [7] with acetic acid and tetrabutylammonium fluoride in THF yields the desired product, CYC682.

Scheme 1: Preparation of CYC682 as described in EP 536936

[1]

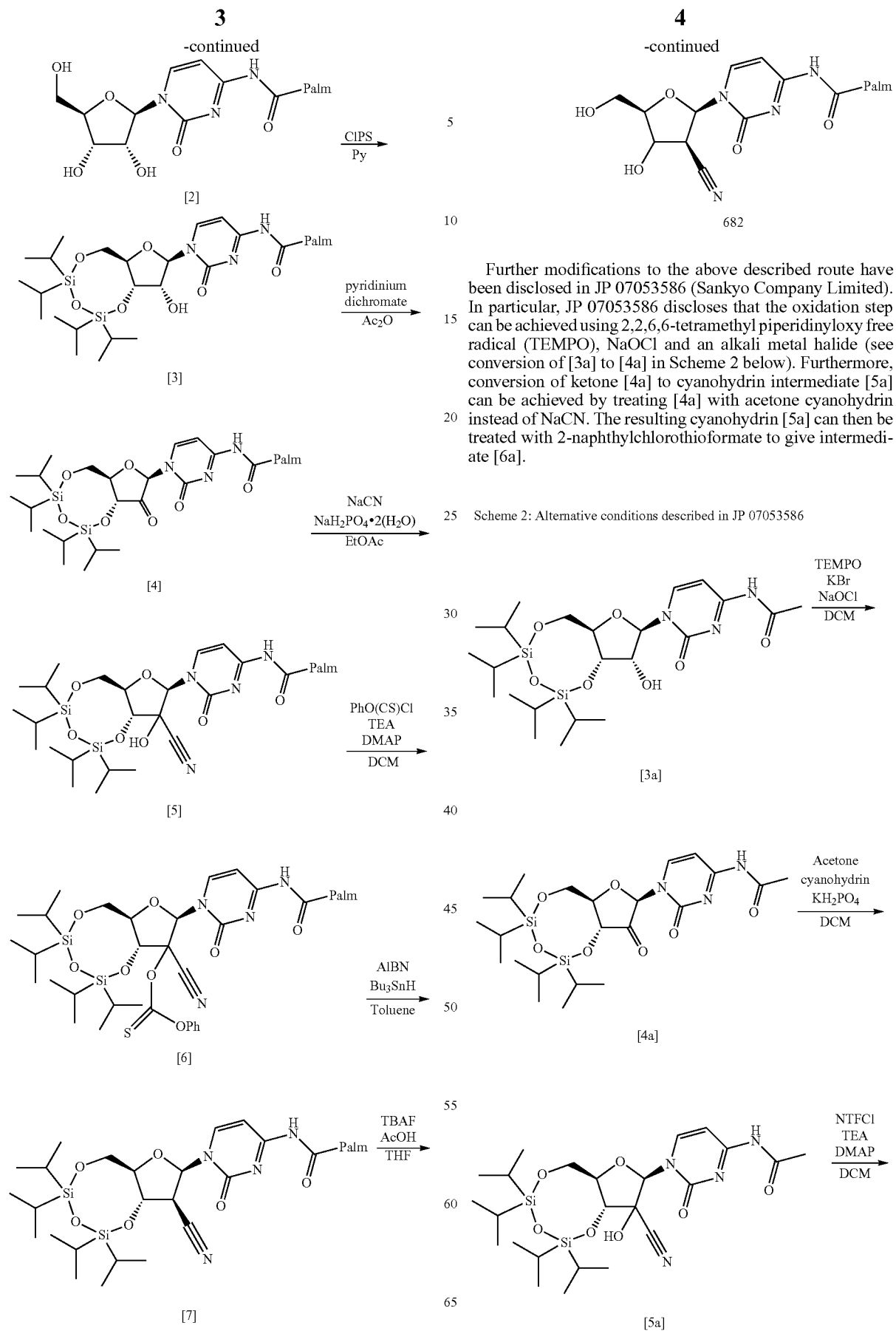

Further modifications to the above described route have been disclosed in JP 07053586 (Sankyo Company Limited). In particular, JP 07053586 discloses that the oxidation step can be achieved using 2,2,6,6-tetramethyl piperidinyloxy free radical (TEMPO), NaOCl and an alkali metal halide (see conversion of [3a] to [4a] in Scheme 2 below). Furthermore, conversion of ketone [4a] to cyanohydrin intermediate [5a] can be achieved by treating [4a] with acetone cyanohydrin instead of NaCN. The resulting cyanohydrin [5a] can then be treated with 2-naphthylchlorothioformate to give intermediate [6a].

Scheme 2: Alternative conditions described in JP 07053586

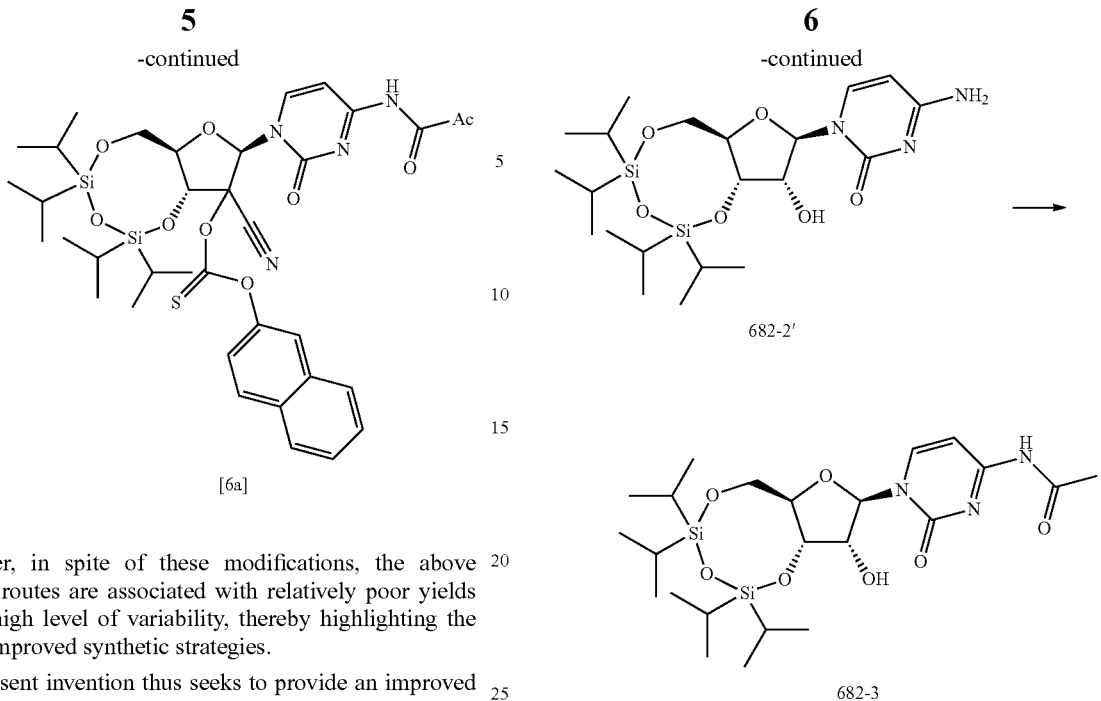

[6a]

However, in spite of these modifications, the above described routes are associated with relatively poor yields and/or a high level of variability, thereby highlighting the need for improved synthetic strategies.

The present invention thus seeks to provide an improved process for preparing CYC682. More specifically, the invention seeks to provide a synthetic route which gives rise to improved yields of CYC682 and/or which is suitable for the large scale preparation of this compound.

STATEMENT OF INVENTION

A first aspect of the invention relates to a process for preparing a compound of formula 682-4,

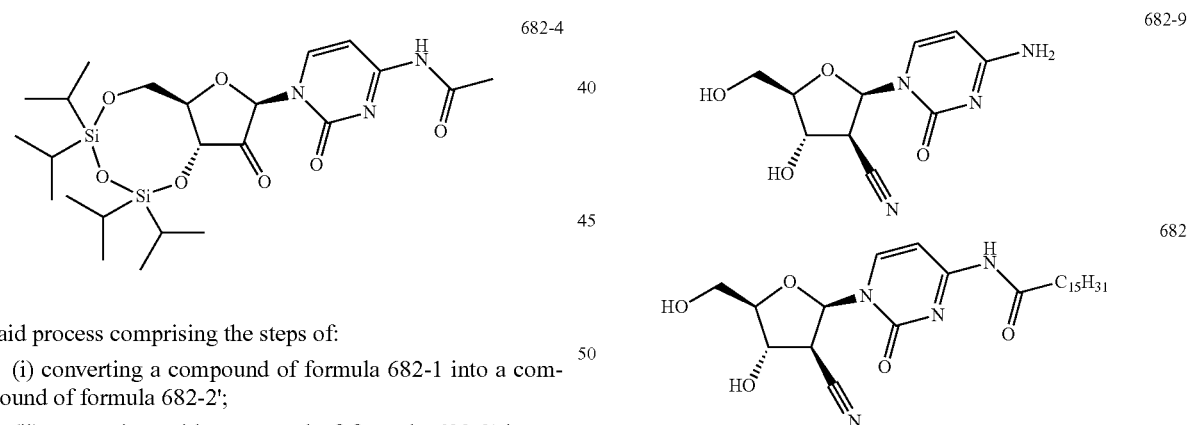

said process comprising the steps of:

(i) converting a compound of formula 682-1 into a compound of formula 682-2';

(ii) converting said compound of formula 682-2' into a compound of formula 682-3; and (iii) converting said compound of formula 682-3 into a compound of formula 682-4

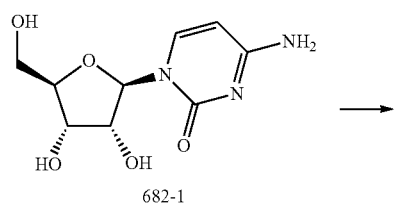

Advantageously, reversal of the first two steps of the synthesis to incorporate the CIPS protecting group prior to the —NH$_2$ protecting group leads to better quality intermediate material 682-4, which forms the substrate for the subsequent reaction with cyanohydrin in the preparation of CYC682.

A second aspect of the invention relates to a process for preparing a compound of formula 682-9 or 682, said process comprising the steps of (A) preparing an intermediate of formula 682-4 as described above;

(B) converting said compound of formula 682-4 to a compound of formula 682-9; and (C) optionally converting said compound of formula 682-9 to a compound of formula 682.

A third aspect of the invention relates to a process for preparing a compound of formula 682-5, said process comprising treating a compound of formula 682-4 with acetone cyanohydrin and NEt$_3$ in heptane

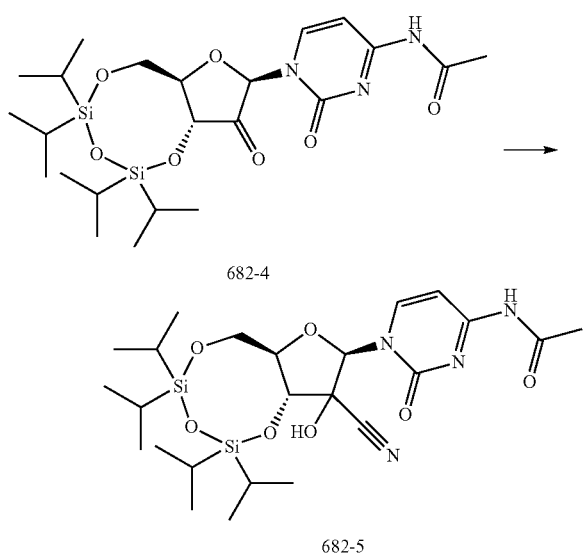

682-4

682-5

Advantageously, the use of acetone cyanohydrin and NEt$_3$ in heptane leads to the improved yield and easier purification of intermediate 682-5 compared to reaction conditions previously known in the art.

A fourth aspect of the invention relates to a process for preparing a compound of formula 682-9 or 682,

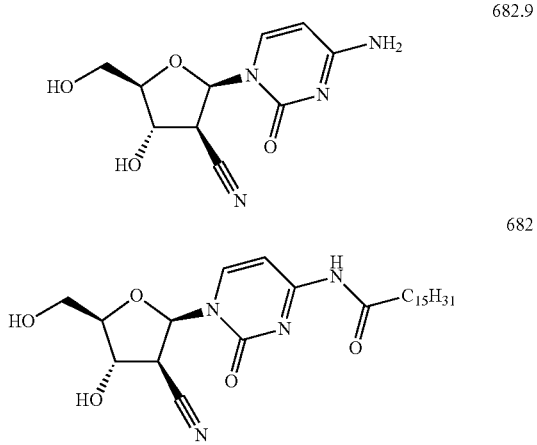

682-9

682 said process comprising the steps of:
(A") preparing an intermediate of formula 682-5 as described above;
(B") converting said compound of formula 682-5 to a compound of formula 682-9; and
(C") optionally converting said compound of formula 682-9 to a compound of formula 682.

DETAILED DESCRIPTION

As described above, a first aspect of the invention relates to a process for preparing a compound of formula 682-4, said process comprising the steps of:
(i) converting a compound of formula 682-1 into a compound of formula 682-2';
(ii) converting said compound of formula 682-2' into a compound of formula 682-3; and
(iii) converting said compound of formula 682-3 into a compound of formula 682-4.

Advantageously, incorporating the CIPS protecting group first in step (i) yields a solid product, 682-2', which can be more easily purified (for example, by washing) to remove unwanted by-products and any excess of the CIPS protecting group reagent. Once purified, the solid 682-2' intermediate so produced is then acylated to give intermediate 682-3, which is subsequently oxidised to give intermediate 682-4. The ability to purify 682-2' in solid form leads to better quality material for use in the subsequent steps of the process, leading to higher yields and improved reproducibility. More particularly, the above route leads to better quality intermediate 682-4, which is the substrate for the subsequent cyanohydrin reaction in the synthesis of CYC682.

In one preferred embodiment of the invention, step (i) comprises treating said compound of formula 682-1 with 1,3-dichloro-1,1,4,4-tetraisopropyldisiloxane (CIPS) in pyridine. Further details of this reaction are reported in Org. Process Dev., 4, 172 (2000); U.S. Pat. No. 6,531,584 B1 (2003); Org. Lett., 8, 55 (2006).

In one preferred embodiment of the invention, step (ii) comprises treating said compound of formula 682-2' with acetic anhydride in EtOH. Alternatively, DMF may be used as the solvent [see Angew. Chem. Int. Ed., 43, 3033 (2004)].

Oxidising agents for converting compound 682-3 to compound 682-4 in step (iii) will be familiar to the skilled artisan. By way of example, the conversion can be achieved by Dess-Martin periodinane oxidation [analogous to methods described in Helv. Chim. Acta, 85, 224 (2002) & J. Org. Chem., 55, 5186 (1990)], Swern oxidation [Org. Process Res. Dev., 4, 172 (2000) & J. Med. Chem., 48, 5504 (2005)], oxidation with pyridinium dichromate or with 2,2,6,6-tetramethyl piperidinyloxy free radical (TEMPO) and NaOCl.

In one particularly preferred embodiment of the invention, step (iii) comprises oxidising said compound of formula 682-3 with 2,2,6,6-tetramethyl piperidinyloxy free radical (TEMPO) in the presence of an alkali metal halide and NaOCl. Further details of this reaction are described in JP 07053586 (Sankyo Company Limited).

Another aspect of the invention relates to a process for preparing a compound of formula 682-9 or 682, said process comprising the steps of:
(A) preparing an intermediate of formula 682-4 as described above;
(B) converting said compound of formula 682-4 to a compound of formula 682-9; and
(C) optionally converting said compound of formula 682-9 to a compound of formula 682.

In one preferred embodiment, step (B) comprises the steps of:

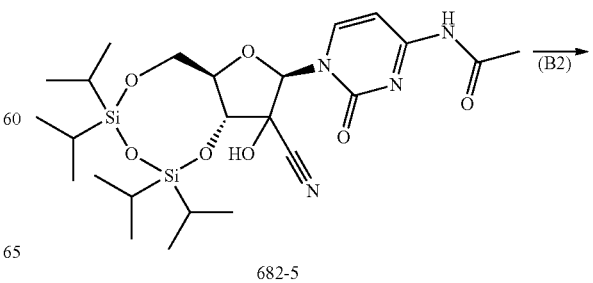

682-5

-continued

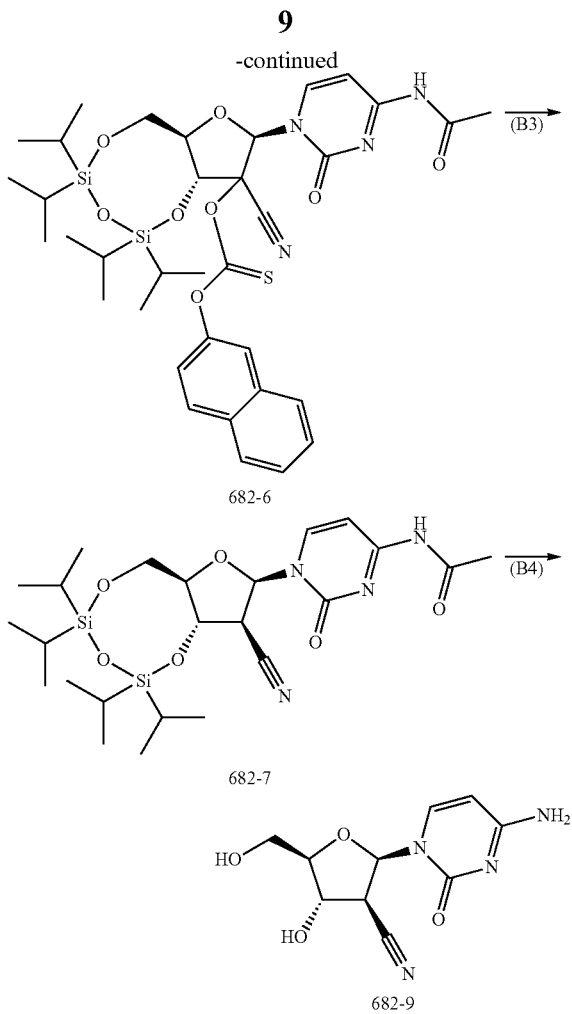

(B1) converting said compound of formula 682-4 into a compound of formula 682-5;

(B2) converting said compound of formula 682-5 into a compound of formula 682-6;

(B3) converting said compound of formula 682-6 into a compound of formula 682-7; and (B4) converting said compound of formula 682-7 into a compound of formula 682-9.

In one preferred embodiment, step (B1) comprises treating said compound of formula 682-4 with NaCN/NaHCO₃ in H₂O/EtOH.

In another preferred embodiment, step (B1) comprises treating said compound of formula 682-4 with NaCN/NaH₂PO₄.2H₂O in ethyl acetate. Further details of this reaction may be found in EP 536936 (Sankyo Company Limited).

In another preferred embodiment, step (B1) comprises treating said compound of formula 682-4 with acetone cyanohydrin/KH₂PO₄ in dichloromethane. Further details of this reaction may be found in JP 07053586 (Sankyo Company Limited).

In one particularly preferred embodiment, step (B1) comprises treating said compound of formula 682-4 with acetone cyanohydrin and NEt₃ in heptane. Further details of this reaction are described below in the second aspect of the invention.

In yet another alternative preferred embodiment, step (B1) comprises treating said compound of formula 682-4 with TMSCN and AlCl₃ in dichloromethane. Further details of this reaction are described in Tet, 60, 9197 (2004).

Preferably, step (B2) comprises treating said compound of formula 682-5 with 2-naphthylchlorothioformate in the presence of NEt₃ and dimethylaminopyridine. Further details of this reaction are described in JP 07053586 (Sankyo Company Limited).

Alternatively, step (B2) comprises treating said compound of formula 682-5 with phenoxylthiocarbonyl chloride in the presence of NEt₃ and dimethylaminopyridine. Further details of this reaction may be found in EP 536936 (Sankyo Company Limited).

Preferably, step (B3) comprises treating said compound of formula 682-6 with tris(trimethylsilyl)silane (TTMSS) and azobisisobutyronitrile (AIBN) in toluene. Further details of the use of this reagent may be found in *J. Org. Chem.*, 53, 3641 (1988) and *Tett. Lett.*, 44, 4027 (2003).

Alternatively, step (B3) comprises treating said compound of formula 682-6 with tributyltin hydride and azobisisobutyronitrile (AIBN) in toluene, as described in EP 536936 (Sankyo Company Limited).

Removal of the CIPS protecting group from said compound of formula 682-7 in step (B4) and subsequent liberation of free base 682-9 may be achieved using methods familiar to the skilled artisan. Preferably, step (B4) comprises treating said compound of formula 682-7 with HCl/MeOH, and then treating the intermediate so produced with a base to form a compound of formula 682-9. Further details of this reaction may be found in EP 536936 (Sankyo Company Limited).

Preferably, step (C) comprises treating said compound of formula 682-9 with palmitic anhydride in a mixture of H₂O/dioxane. Other suitable conditions for this conversion will be familiar to the skilled artisan.

A further aspect of the invention relates to a process for preparing a compound of formula 682-5, said process comprising treating a compound of formula 682-4 with acetone cyanohydrin and NEt₃ in heptane

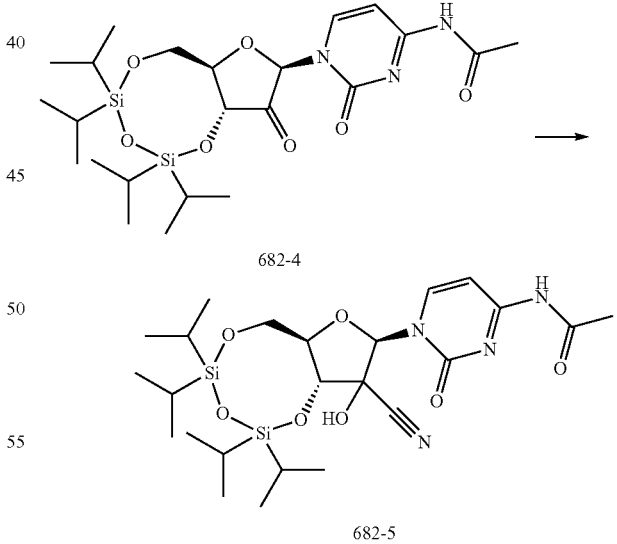

Advantageously, the use of acetone cyanohydrin and NEt₃ in heptane leads to the improved yield and easier purification of intermediate 682-5 compared to reaction conditions previously known in the art.

Prior art conditions for this conversion typically involve the use of NaCN or acetone cyanohydrin and triethylamine in a 2-phase reaction mixture (for example, water/ethyl acetate)

which gives rise to an equilibrium between ketone starting material 682-4 and two possible cyanohydrin isomers. In contrast, the use of cyanohydrin and NEt₃ in heptane favours the formation of just one of the two possible cyanohydrin products; the desired cyanohydrin product is insoluble in heptane and precipitates out of solution, whilst the other isomer and starting ketone 682-4 remain in solution. This precipitation drives the equilibrium towards completion in accordance with Le Chatelier's Principle, thereby leading to improved yields of the desired cyanohydrin. Moreover, the formation of a solid allows for the easier processing of intermediate 682-5.

In one preferred embodiment, the process further comprises the step of preparing said compound of formula 682-4 from a compound of formula 682-3

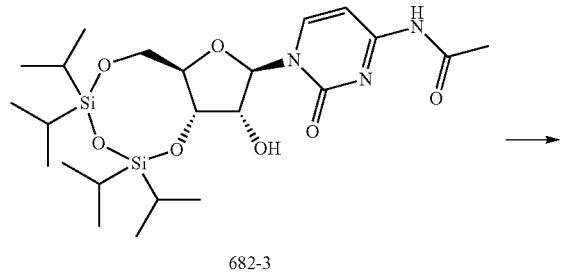

682-3

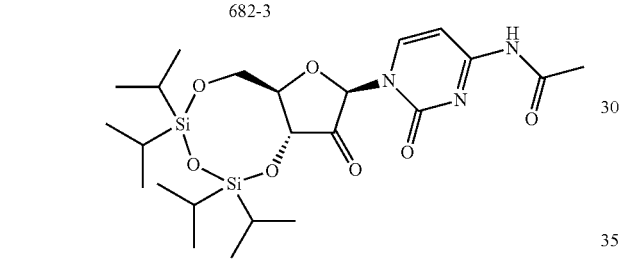

682-4

Suitable oxidation conditions are as described above for the first aspect of the invention. More preferably, the process comprises reacting a compound of formula 682-3 with 2,2,6,6-tetramethyl piperidinyloxy free radical (TEMPO) and NaOCl.

In one preferred embodiment, the process further comprises the step of preparing said compound of formula 682-3 from a compound of formula 682-2

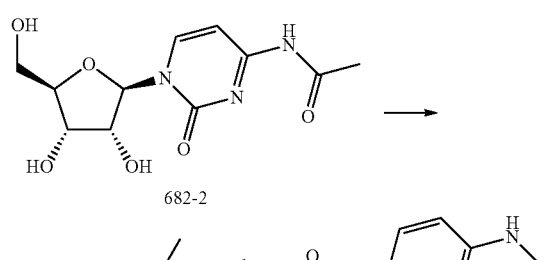

682-2

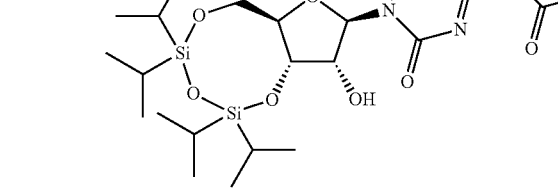

682-3

More preferably, the process comprises reacting said compound of formula 682-2 with 1,3-dichloro-1,1,4,4-tetraisopropyldisiloxane (CIPS) in pyridine. Suitable conditions for this conversion are as described above for the first aspect of the invention.

In one preferred embodiment, the process further comprises the step of preparing said compound of formula 682-2 from a compound of formula 682-1

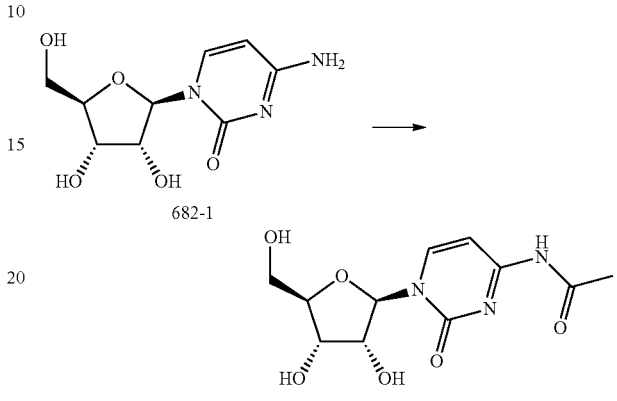

682-1

682-2

More preferably, the process comprises reacting said compound of formula 682-1 with Ac₂O in EtOH. Suitable conditions for this conversion are as described above for the first aspect of the invention.

In one preferred embodiment, the process further comprises the step of preparing said compound of formula 682-3 from a compound of formula 682-2'

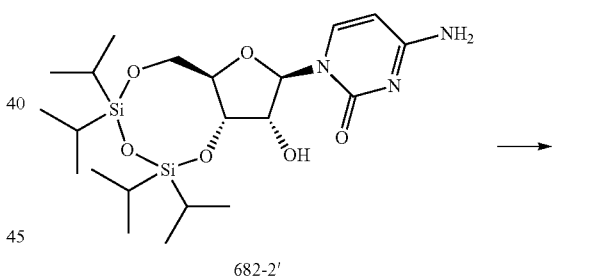

682-2'

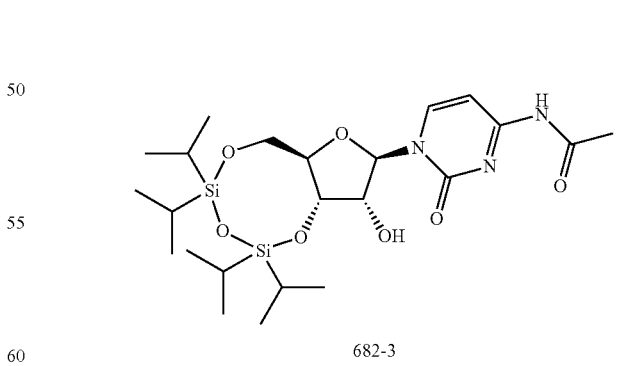

682-3

More preferably, the process comprises reacting said compound of formula 682-T with Ac₂O in EtOH.

In one preferred embodiment, the process further comprises the step of preparing said compound of formula 682-2' from a compound of formula 682-1

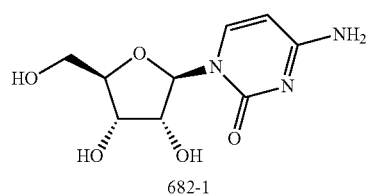

682-1

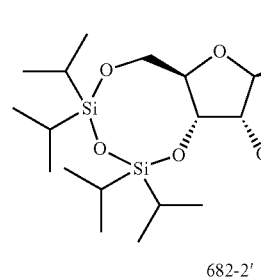

682-2'

More preferably, the process comprises reacting a compound of formula 682-1 with 1,3-dichloro-1,1,4,4-tetraisopropyldisiloxane (CIPS) in pyridine.

A further aspect of the invention relates to a process for preparing a compound of formula 682-9 or 682,

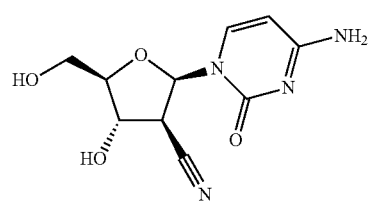

682-9

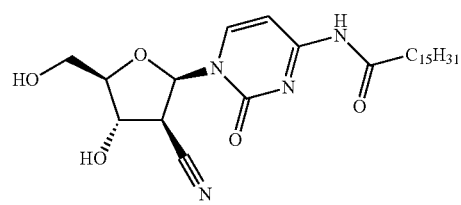

682 said process comprising the steps of:
(A") preparing an intermediate of formula 682-5 as described above;
(B") converting said compound of formula 682-5 to a compound of formula 682-9; and
(C") optionally converting said compound of formula 682-9 to a compound of formula 682.

Preferably, for this embodiment, step (B") comprises the steps of:

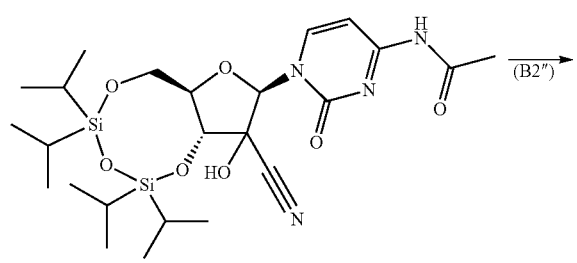

682-5

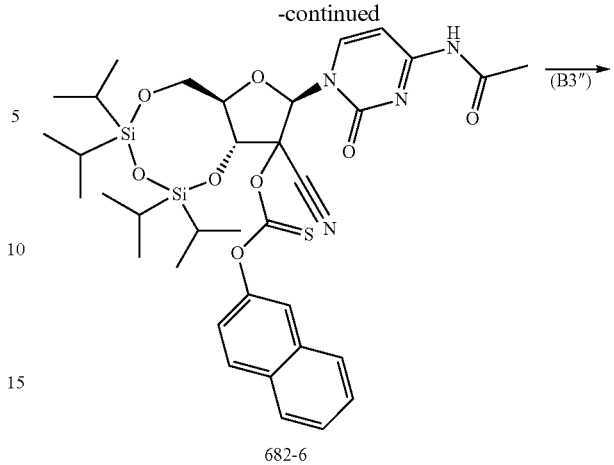

682-6

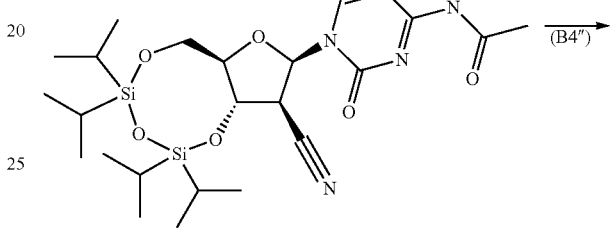

682-7

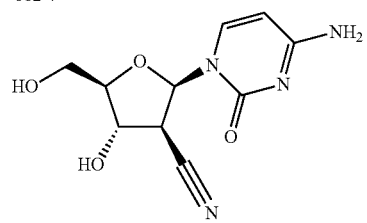

682-9

(B2") converting said compound of formula 682-5 into a compound of formula 682-6;
(B3") converting said compound of formula 682-6 into a compound of formula 682-7; and
(B4") converting said compound of formula 682-7 into a compound of formula 682-9.

Preferably, step (B2") comprises treating said compound of formula 682-5 with 2-naphthylchlorothioformate in the presence of NEt$_3$ and dimethylaminopyridine. Suitable conditions for this step are as described above for the first aspect of the invention.

Preferably, step (B3") comprises treating said compound of formula 682-6 with tris(trimethylsilyl)silane (TTMSS) and azobisisobutyronitrile (AIBN) in toluene. Suitable conditions for this step are as described above for the first aspect of the invention.

Preferably, step (B4") comprises treating said compound of formula 682-7 with HCl/MeOH, and then treating the intermediate so produced with a base to form a compound of formula 682-9. Suitable conditions for these steps are as described above for the first aspect of the invention.

Preferably, step (C") comprises treating said compound of formula 682-9 with palmitic anhydride in a mixture of H$_2$O/dioxane.

The present invention is further described by way of non-limiting examples, and with reference to the following figures, wherein;

FIG. 1 shows synthesis of CYC682 via Route 1, a modification of the prior art procedure.

FIG. 2 shows synthesis of CYC682 via Route 1a, in accordance with a preferred embodiment of the invention.

EXAMPLES

Step 1: 682-1→682-2'

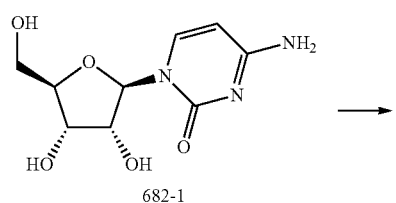
682-1

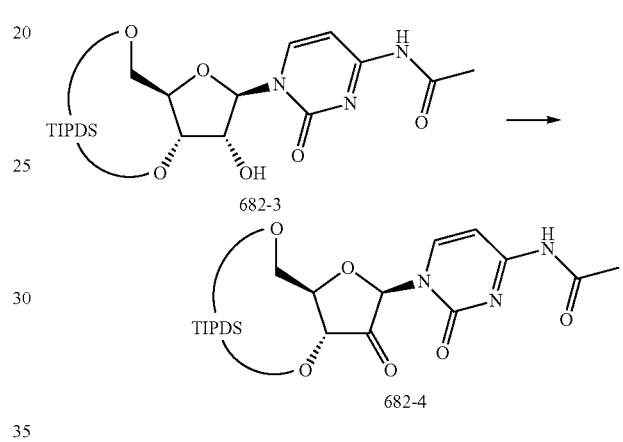
682-2'

682-3

682-4

*Org. Process Dev.*, 4, 172 (2000); U.S. Pat. No. 6,531,584 B1 (2003); *Org. Lett.*, 8, 55 (2006). Cytidine (8.0 g, 32.89 mmol) was pre-dried by azeotroping with pyridine (2×15 ml), then suspended in pyridine (22 ml) and the vessel purged with argon. 1,3-Dichloro-1,1,4,4-tetraisopropyldisiloxane (12.0 ml, 35.40 mmol) was added dropwise at room temperature over a period of 20 min. A mild exotherm to 32° C. was observed. A heavy white precipitate gradually settled at the bottom of the flask. This was broken up with vigorous stirring and the resulting heavy suspension stirred overnight. The mixture was poured into water (200 ml) and extracted with EtOAc (3×200 ml). The combined organics were washed (brine), dried (MgSO$_4$), filtered and evaporated to a white solid. This was triturated with heptane, filtered and washed with heptane (100 ml) followed by light pet ether (2×50 ml). 13.46 g (84%) obtained. In the last stage of the work up, isopropyl acetate may be substituted for heptane.

Step 2: 682-2'→682-3

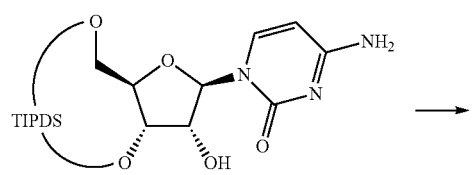
682-2'

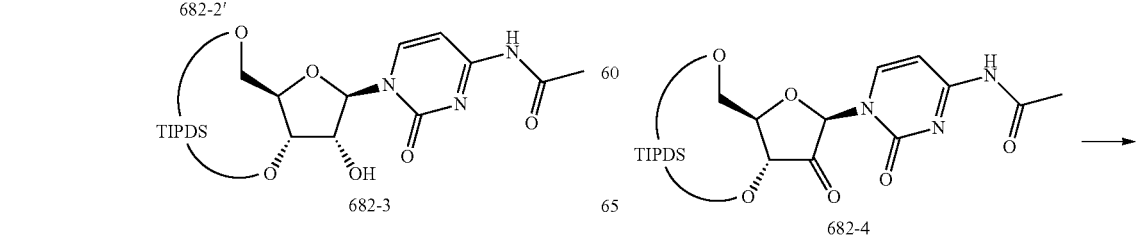
682-3

682-2' (10.0 g, 20.59 mmol) was suspended in ethanol (200 ml) and acetic anhydride (6.9 ml, 72.06 mmol) added dropwise (no exotherm). The mixture was heated (oil bath 65° C.—internal temp 50-53° C.) for 2 h. Tlc (7% MeOH/DCM) showed product with only trace of starting material. A further 3 ml of acetic anhydride was added (no exotherm) and heating continued a further 1.5 h. Tlc showed no starting material. The mixture was cooled to room temperature and the EtOH evaporated on RV. 5% NaHCO$_3$ (100 ml) was added (CO$_2$↑) and the mixture extracted with 1:1 TBDME/heptane (3×100 ml). The combined organics were washed (brine), dried (MgSO$_4$), filtered and evaporated to a white foam (10.43 g, 96%).

Step 3: 682-3→682-4

682-3 (8.0 g, 15.15 mmol) was dissolved in DCM (120 ml) and cooled to 10° C. in an ice-bath. Dess-Martin periodinane (12.58 g, 28.78 mmol) was added in small portions and the addition funnel rinsed with DCM (20 ml). The resulting cloudy solution stirred with cooling for 10 min, then at room temperature overnight. The mixture was diluted with Et$_2$O (450 ml) and washed with aq NaHCO$_3$ (200 ml) in which Na$_2$S$_2$O$_3$.5H$_2$O (38.5 g) had been dissolved. The aqueous phase was extracted with Et$_2$O (200 ml). The combined organics were washed (sat NaHCO$_3$, followed by brine), dried (MgSO$_4$) filtered and evaporated to a crisp white foam. NMR showed ca.7.5% of starting material remaining. The crude product was redissolved in DCM (150 ml) and treated with a further 2.5 g (5.89 mmol) of Dess-Martin periodinane as before. The reaction mixture was worked up as before (using 9 g Na$_2$S$_2$O$_3$.5H$_2$O) to give 7.54 g (95%) of the desired product as a white foam.

Step 4: 682-4→682-5

682-4

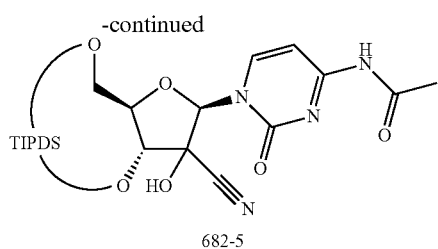

682-5

682-4 (700 mg, 1.33 mmol) was partially dissolved in heptane (7 ml) to give a hazy solution. Acetone cyanohydrin (0.25 ml, 2.66 mmol) was added in a steady stream, followed by dropwise addition of triethylamine (19 μl, 0.13 mmol). The mixture was stirred at room temperature, gradually becoming more cloudy. After ca. 20 min the reaction mixture was a thick, paste-like suspension. LCMS after 1 h showed no starting material. The mixture was cooled in an ice bath and filtered. The collected white solid was washed with cold heptane (ca. 15 ml) followed by light pet ether (ca. 5 ml). The product was dried under vacuum at 40° C. 673 mg (91%) obtained.

Step 5: 682-5→682-6

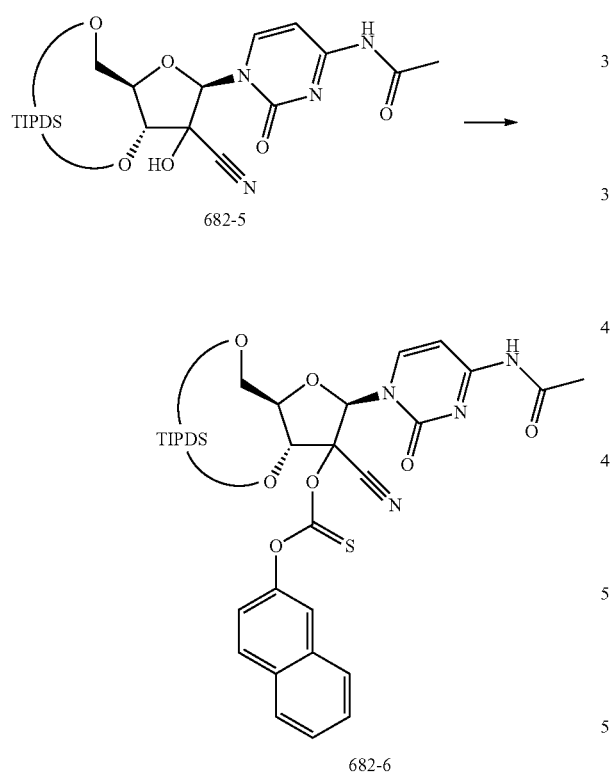

A solution of 2-naphthyl chlorothioformate in toluene (2-NTF) (25% solution, 1.82 kg/kg 682-5) is added to 682-5 in dichloromethane (10 L/kg 682-5) and 4-dimethylaminopyridine (0.022 kg/kg 682-5) at, or below 5° C. Triethylamine (0.22 kg/kg 682-5) at 0° to 10° C., is added slowly to the reaction mixture at a rate to maintain the temperature at 10° C., or below. The mixture is maintained at 0° to 10° C. and monitored by HPLC. The reaction is continued until the 682-5 content is ≤2.0%. At the completion of the reaction, 1% w/w aqueous sodium dihydrogen phosphate (10 kg/kg 682-5) is added at a rate to maintain the temperature at 10° to 25° C. The phases are separated and the aqueous phase extracted with additional dichloromethane (4.5 L/kg 682-5). After phase split, the organic phases are washed with a single low pyrogen water (10 L/kg 682-5) charge, combined and transferred for distillation with a dichloromethane line wash. The organic phase is concentrated under reduced pressure at not more than 30° C. Methanol (3 L/kg 682-5) is charged and concentration continued. Additional methanol is charged (10 L/kg 682-5) and the product granulated for at least 1 hour at, or below 5° C. The product is isolated by centrifugation in up to two loads. Each load is washed with cold methanol (1.5 L/kg 682-5) at 0° to 5° C., prior to drying under vacuum at up to 45° C., to constant weight.

Step 6: 682-6→682-7

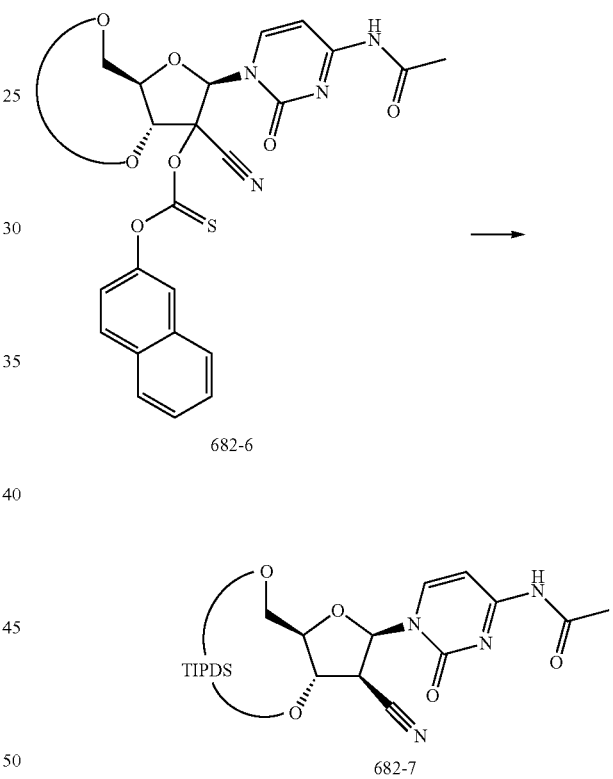

The radical initiator Vazo67 (2,2'-azobis[2-methylbutyronitrile]) (0.05 kg/kg 682-6) and tris(trimethylsilyl)silane (TTMSS) (0.41 kg/kg 682-6) are added to the intermediate 682-6 in toluene (4.5 L/kg 682-6). The reaction mixture is heated to 70° C. and agitated at 65° to 75° C. for at least 1 hour, prior to monitoring. The mixture is monitored by HPLC. The reaction is continued until the 682-6 content is ≤2.0%. Additional initiator and TTMSS can be added if required. After reaction completion is achieved, the mixture is added slowly to ethylcyclohexane (20 L/kg 682-6) at 65° to 75° C. The reaction mixture is cooled to 0° to 5° C. over at least 2.5 hours and held at this temperature. The resultant solid is isolated by centrifugation in up to three loads. Each load is washed with a cold ethylcyclohexane (1 L/kg 682-6) at 0° to 5° C. The product is dried under vacuum at up to 45° C., to constant weight.

Step 7: 682-7→682-8

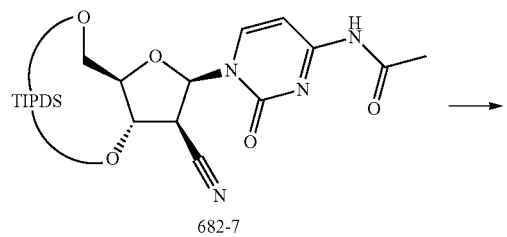

682-7

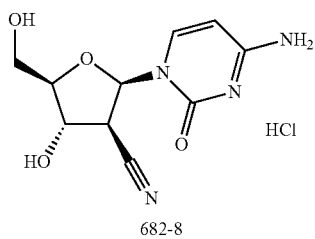

682-8

To establish hydrolysis, 682-7 is dissolved in methanol (2.34 L/kg 682-7) and hydrochloric acid (36%, 0.48 L/kg 682-7) at 48° to 52° C. A 682-8 seed is prepared by treating 682-9 (5 g/kg 682-7) with hydrochloric acid (29 mL/kg 682-7) in methanol (140 mL/kg 682-7), prior to charging to the reaction mixture. The reaction mixture is heated at 53° C. to 60° C. for at least 2 hours and monitored by HPLC. The reaction is continued until the peak at retention time ca 5.25 is ≤12.0%. At the completion of the reaction, the mixture is cooled to 10° C. to 15° C. over at least 100 minutes. Ethyl acetate (10 L/kg 682-7) is added over at least 25 minutes at 10° C. to 15° C., and the mixture cooled to 0° C. to 5° C. over at least 30 minutes. The mixture is granulated at less than 5° C. for at least 1 hour. The product is isolated by centrifugation in up to two loads and each load washed with a cold mixture of methanol (0.38 L/kg 682-7) and ethyl acetate (1.11 L/kg 682-7) at 0° to 5° C. The product is dried under vacuum at up to 45° C., to constant weight.

Step 8: 682-8→682-9

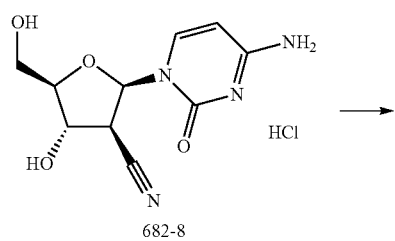

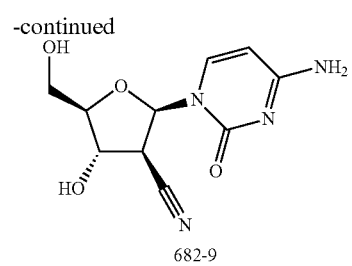

682-9

The hydrochloride salt 682-8 is neutralised by adding triethylamine (0.41 kg/kg 682-8) to a suspension of 682-8 in a methanol (3.9 L/kg 682-8): dichloromethane (10 L/kg 682-8) mixture at 15° to 30° C. Dissolution occurs on addition of the triethylamine. The reaction mixture is agitated at 15° to 30° C. for at least 10 minutes and the pH of a sample checked after dilution with water. It is expected to be in the range pH 9 to 9.5. The intermediate 682-9 may undergo epimerization at high pH. Acetic acid (0.25 kg/kg 682-8) is added slowly with agitation, at a rate to maintain the temperature at less than 30° C., to adjust the pH range to 4.0 to 4.5 and induce crystallisation. Additional acetic acid may be added if required. The mixture is then diluted with dichloromethane (25 L/kg 682-8) and cooled to 0° C. to 5° C. The mixture is stirred at 0° C. to 5° C. for at least 1 hour, the product isolated by centrifugation in up to two loads. Each load is washed with a cold mixture of methanol (0.63 L/kg 682-8) and dichloromethane (4.4 L/kg 682-8). The product is dried under vacuum at up to 45° C., to constant weight.

Step 9: 682-9→682

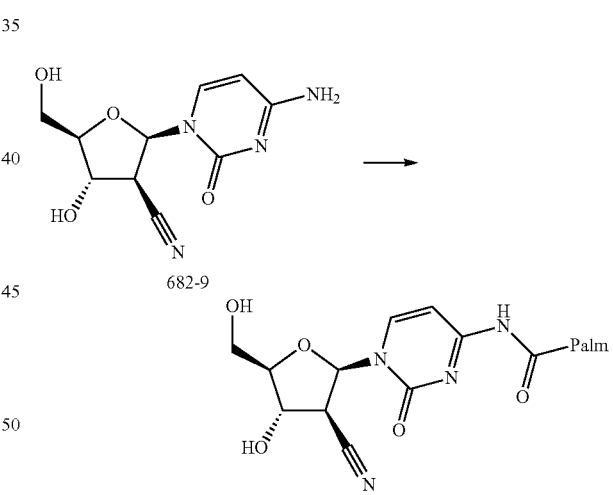

682 can be obtained in accordance with the methods disclosed in Examples 1-4 of EP 536936. The intermediate 682-9 is converted to CYC682 and is initially isolated as Form K which is a methanol solvate. Form K is converted to Form B which is a hemihydrate by a suspension form change reaction. Form K or Form B can be further purified by recrystallisation. The recrystallisation yields Form K which is then converted, or reconverted to Form B.

(i) 682: Form K

Palmitic anhydride (3.53 kg/kg 682-9) is added to a mixture of 682-9 in 1,4-dioxane (20 L/kg 682-9) and low pyrogen water (1.0 L/kg 682-9) and the reaction mixture is heated to 80° to 90° C. (target range 80° to 85° C.). The reaction is monitored by HPLC and continued until the 682-9 content is 52.0%. At the completion of the reaction, the mixture is hot filtered and the filter washed with 1,4-dioxane (10 L/kg 682-9) at 70° to 90° C. The resultant combined filtrate is concentrated to less than 30% of its original volume (7.3 L/kg 682-9) at or below 60° C. (target internal temperature 45° C. to 55° C., or less). The water content is checked by Karl Fischer titration. If the water content is <2%, additional dioxane is added and the distillation repeated. If required, 1,4-dioxane is added to dilute the mixture to 30% of the original volume. Ethylcyclohexane (48.3 L//kg 682-9) and 1,4-dioxane (3.66 L/kg 682-9) are added and the temperature adjusted into the range 43° to 47° C. Methanol (3.23 L/kg 682-9) is added at 40° to 45° C. over at least 5 minutes.

In a separate reactor CYC682 seed crystals (Form B) (10 g/kg 682-9) are added to a mixture of ethylcyclohexane (1333 mL/kg 682-9), 1,4-dioxane (177 mL/kg 682-9) and methanol (89 mL/kg 682-9) (15:2:1 v/v/v). The resultant mixture is stirred at 20° to 25° C. for at least 1 hour, then added to the crude reaction solution at 40° to 45° C. After crystallisation of the Form K occurs, the reaction mixture is stirred at 40° to 45° C. for at least a further 30 minutes. The reaction mixture is cooled to 20° to 23° C. over at least 120 minutes, and held in the range 20° to 23° C. for at least 1 hour. The resultant solid is isolated by centrifugation in up to two loads and each load washed with a mixture of ethylcyclohexane (7.5 L/kg 682-9), 1,4-dioxane (1.0 L/kg 682-9) and methanol (0.5 L/kg 682-9) at 0° to 5° C. The product is dried under vacuum at 35° to 40° C., to constant weight to yield CYC682 (Form K).

(ii) 682: Form B

CYC682 (Form K) is suspended in methyl acetate (8.9 L/kg CYC682) containing approximately 1.5 to 2% low pyrogen water (169.3 mL/kg CYC682). The suspension is stirred at 20° to 25° C. (target 22° to 24° C.) for 1.5 hours and undergoes form conversion. The product is isolated by Nutsche filtration and washed with a mixture of methyl acetate (2.2 L/kg CYC682) and low pyrogen water (42.3 mL/kg CYC682) 20° to 25° C. The product is dried under vacuum at or below 40° C., to constant weight, to yield CYC682 (Form B).

Recrystallisation of CYC682 (Form K or B)

CYC682 (Form K or B) is suspended in a mixture of 1,4-dioxane (3.33 L/kg CYC682) and ethylcyclohexane (25 L/kg CYC682) and the mixture adjusted into the range 43° to 47° C. Methanol (1.66 L/kg CYC682) is added at 40° to 50° C. over at least 5 minutes to achieve dissolution. Additional heating up to 60° C. may be required to achieve dissolution of CYC682 Form B.

In a separate reactor CYC682 seed crystals (4 to 15 g/kg CYC682) are added to a mixture of ethylcyclohexane, 1,4-dioxane and methanol (15:2:1 v/v/v) as in section (i) above. The resultant mixture is stirred at 20° to 25° C. for at least 1 hour, then added to the crude reaction solution at 40° to 45° C. After crystallisation of the Form K occurs, the reaction mixture is stirred at 40° to 45° C. for at least a further 30 minutes. The reaction mixture is cooled to 20° to 23° C. over at least 120 minutes, and held in the range 20° to 23° C. for at least 1 hour. The resultant solid is isolated by centrifugation in up to two loads and each load washed with a mixture of ethylcyclohexane (3.852 L/kg CYC682), 1,4-dioxane (0.514 L/kg CYC682) and methanol (257 mL/kg CYC682) at 0° to 5° C. The product is dried under vacuum at 35° to 40° C., to constant weight to yield CYC682 (Form K).

Comparative Studies

Studies by the Applicant have shown that the process steps as presently claimed lead to improved yields over methodology previously used in the art. By way of example, Table 1 below compares the yields for each step in Route 1 (see FIG. 1; prior art methodology) and Route 1a (see FIG. 2; in accordance with the invention).

TABLE 1

| | Comparison of yields for Route 1 and Route 1a | | | | | | | | | | |
|---|---|---|---|---|---|---|---|---|---|---|---|
| | →2 | →3 | →4 | →5 | →6 | →7 | →8 | →9 | →K | →B | Tot. |
| Route 1 | 98 | | | 38 | 90 | 91 | 85 | 97 | 89 | 89 | 19.9 |
| Route 1a | 86 | 99 | 95 | 92 | 90 | 91 | 85 | 97 | 89 | 89 | 39.8 |

Table 1 shows that reversal of the first two steps in the synthesis, (Route 1a, i.e. incorporating the CIPS protecting group prior to the acylation step), and the use of acetone cyanohydrin/heptane in the cyanation step gives rise to intermediate 682-5 in high yield. By way of comparison, performing the acylation step prior to incorporating the CIPS protecting group (Route 1), and using standard cyanation conditions known in the art (e.g. NaCN, NaHCO$_3$ in H$_2$O/EtOAC gives rise to a much lower yield 682-5 (38%). Overall, a comparison of the two routes gives 19.9% CYC682 for Route 1, compared to 39.8% CYC682 for Route 1a.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:

1. A process for preparing a compound of formula 682-4,

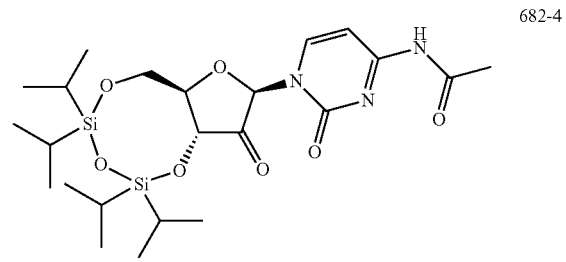 [SMILES: CC(=O)Nc1ccn([C@@H]2O[C@@H]3CO[Si](C(C)C)(C(C)C)O[Si](C(C)C)(C(C)C)O[C@H]3C2=O)c(=O)n1]

said process comprising the steps of:
(i) converting a compound of formula 682-1 into a compound of formula 682-2' by treating said compound of formula 682-1 with 1,3-dichloro-1,1,4,4-tetraisopropyldisiloxane (CIPS) in pyridine;

(ii) converting said compound of formula 682-2' into a compound of formula 682-3 by treating said compound of formula 682-2' with acetic anhydride in EtOH; and
(iii) converting said compound of formula 682-3 into a compound of formula 682-4 by treating said compound of formula 682-3 with an oxidizing reagent said process comprising the steps of:
(A) preparing an intermediate of formula 682-4 according to claim 1;
(B) converting said compound of formula 682-4 to a compound of formula 682-9 comprising the steps of:

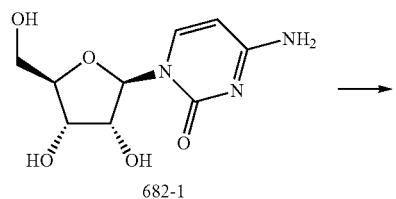

682-1

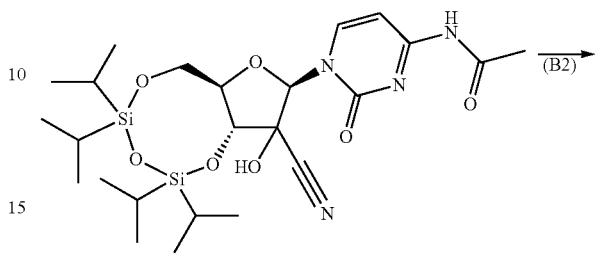

682-5

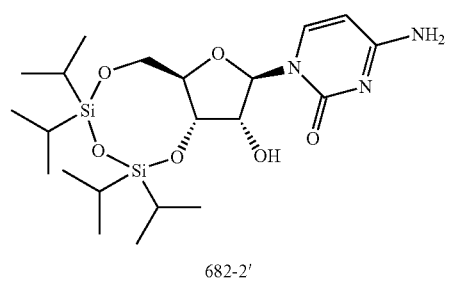

682-2'

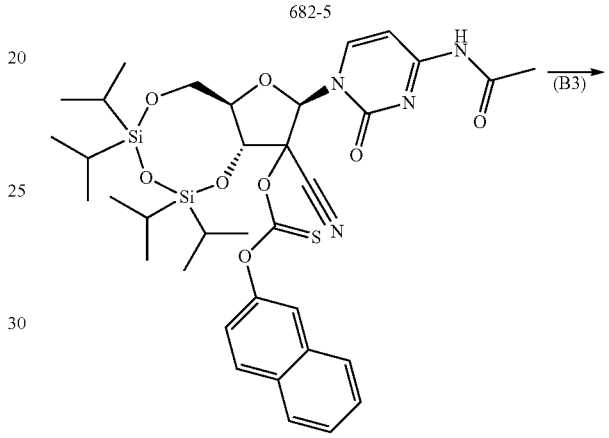

682-6

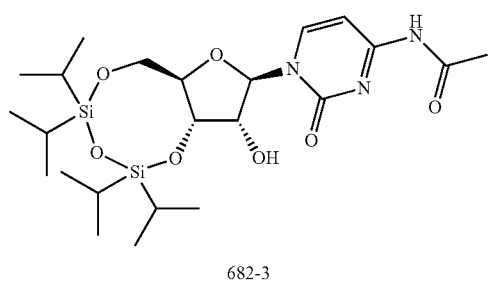

682-3

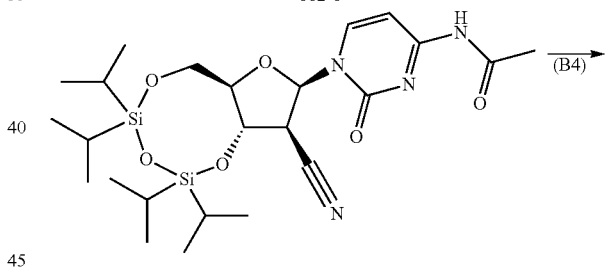

682-7

2. A process for preparing a compound of formula 682-9 or 682,

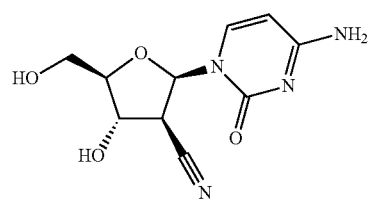

682-9

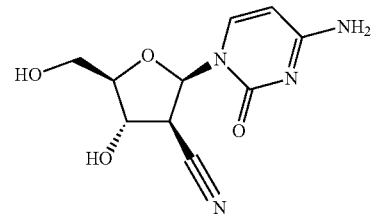

682-9

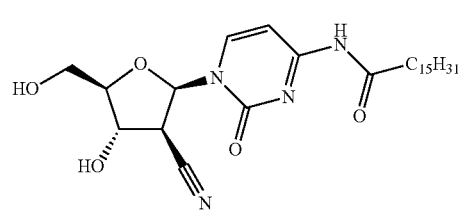

682

(B1) converting said compound of formula 682-4 into a compound of formula 682-5 by treating said compound of formula 682-4 with NaCN/NaHCO$_3$ in H$_2$O/EtOH or by treating said compound of formula 682-4 with acetone cyanohydrin and NEt$_3$ in heptane;
(B2) converting said compound of formula 682-5 into a compound of formula 682-6 by treating said compound of formula 682-5 with 2-naphthylchlorothioformate in the presence NEt$_3$ and dimethylaminopyridine;

(B3) converting said compound of formula 682-6 into a compound of formula 682-7 by treating said compound of formula 682-6 with tris(trimethylsilyl)silane (TT-MSS) and azobisisobutyronitrile (AIBN) in toluene; and (B4) converting said compound of formula 682-7 into a compound of formula 682-9 by treating said compound of formula 682-7 with HCl/MeOH, and then treating the intermediate so produced with a base to form a compound of formula 682-97; and (C) optionally converting said compound of formula 682-9 to a compound of formula 682 comprising treating said compound of formula 682-9 with palmitic anhydride in a mixture of H₂O/dioxane.

3. A process for preparing a compound of formula 682-5, said process comprising treating a compound of formula 682-4 with acetone cyanohydrin and NEt₃ in heptane

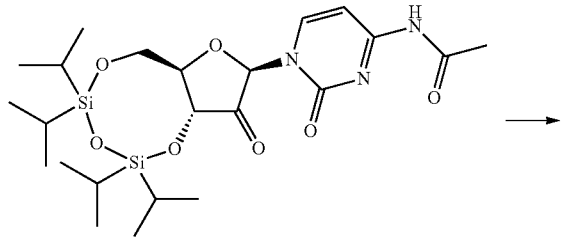

682-4

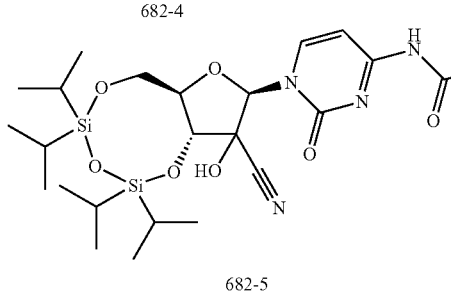

682-5

4. A process according to claim 3 which further comprises the step of preparing said compound of formula 682-4 from a compound of formula 682-3 by reacting a compound of formula 682-3 with 2,2,6,6-tetramethyl piperidinyloxy free radical (TEMPO) and NaOCl

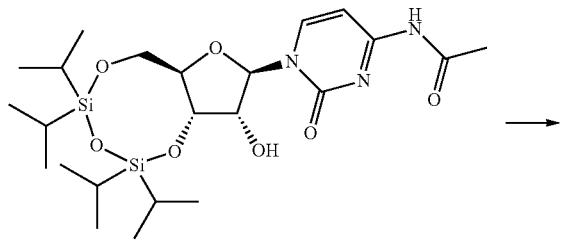

682-3

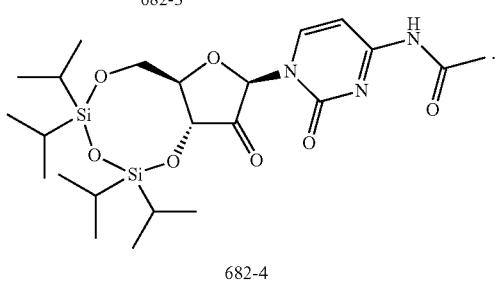

682-4

5. A process according to claim 4 which further comprises the step of preparing said compound of formula 682-3 from a compound of formula 682-2 by reacting said compound of formula 682-2 with 1,3-dichloro-1,1,4,4-tetraisopropyldisiloxane (CIPS) in pyridine

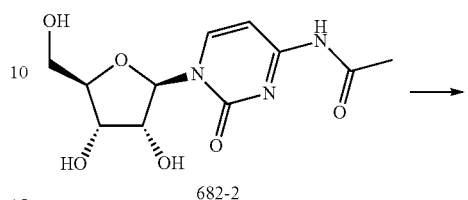

682-2

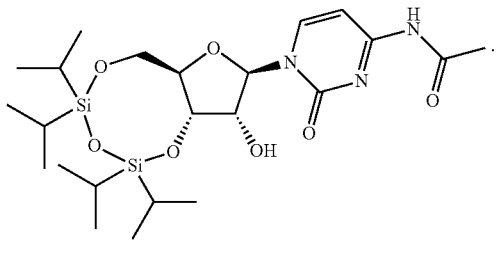

682-3

6. A process according to claim 5 which further comprises the step of preparing said compound of formula 682-2 from a compound of formula 682-1 by reacting said compound of formula 682-1 with Ac₂O in EtOH

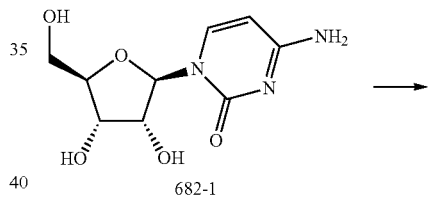

682-1

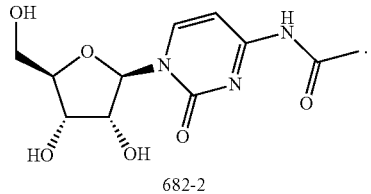

682-2

7. A process according to claim 4, which further comprises the step of preparing said compound of formula 682-3 from a compound of formula 682-2' by reacting said compound of formula 682-2' with Ac₂O in EtOH

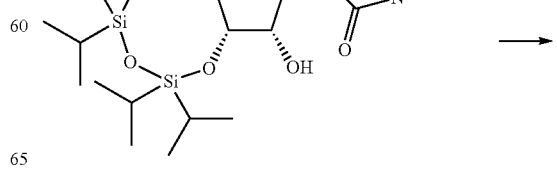

682-2'

-continued

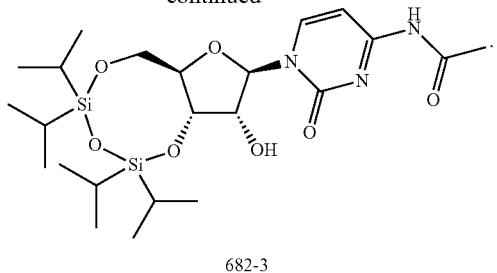

682-3

8. A process according to claim 7 which further comprises the step of preparing said compound of formula 682-2' from a compound of formula 682-1 by reacting a compound of formula 682-1 with 1,3-dichloro-1,1,4,4-tetraisopropyldisiloxane (CIPS) in pyridine

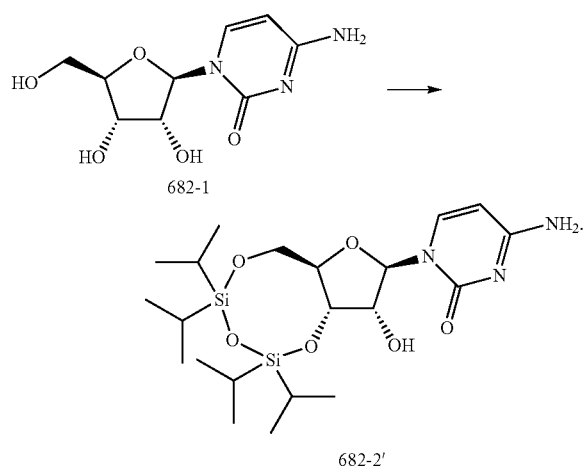

9. A process for preparing a compound of formula 682-9 or 682,

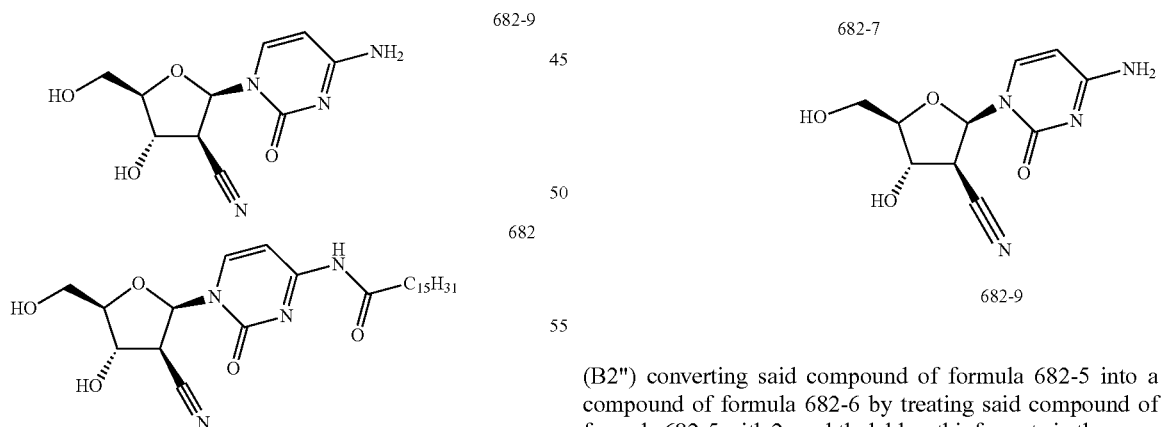

said process comprising the steps of:
(A") preparing an intermediate of formula 682-5 according to any one of claims 3, 4, 5, 6, 7 and 8;
(B") converting said compound of formula 682-5 to a compound of formula 682-9; and
(C") optionally converting said compound of formula 682-9 to a compound of formula 682.

10. A process according to claim 9 wherein step (B") comprises the steps of:

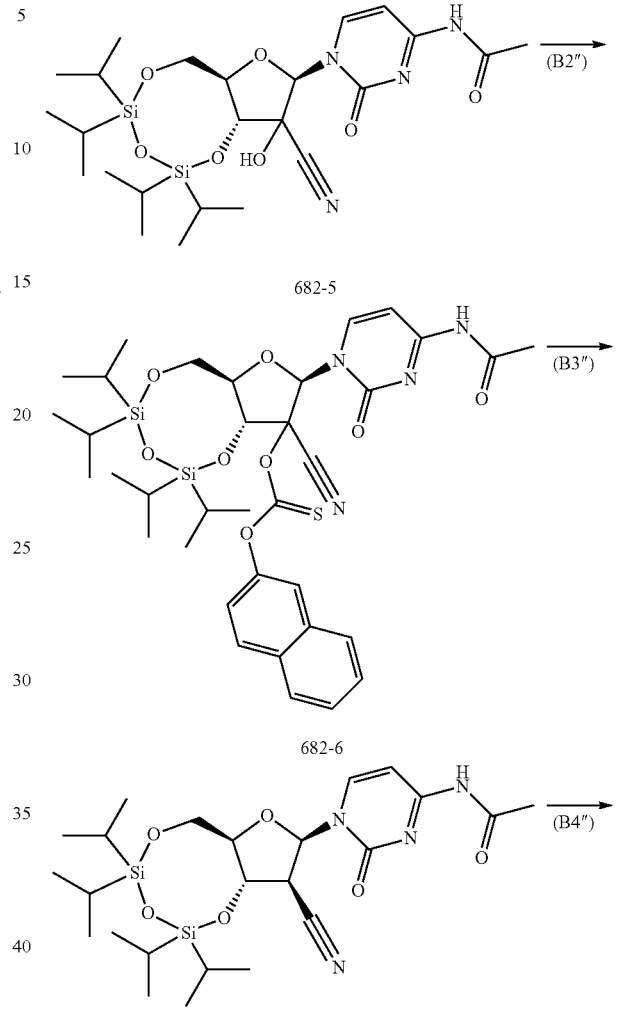

(B2") converting said compound of formula 682-5 into a compound of formula 682-6 by treating said compound of formula 682-5 with 2-naphthylchlorothioformate in the presence OfNEt₃ and dimethylaminopyridine;

(B3") converting said compound of formula 682-6 into a compound of formula 682-7 by treating said compound of formula 682-6 with tris(trimethylsilyl)silane (TTMSS) and azobisisobutyronitrile (AIBN) in toluene; and (B4") converting said compound of formula 682-7 into a compound of formula 682-9 by treating said compound of formula 682-7 with HCl/MeOH, and then treating the intermediate so produced with a base to form a compound of formula 682-9.

11. A process according to claim 9 wherein step (C") comprises treating said compound of formula 682-9 with palmitic anhydride in a mixture of H₂O/dioxane.

12. A process according to claim 10 wherein step (C") comprises treating said compound of formula 682-9 with palmitic anhydride in a mixture of H₂O/dioxane.

13. A compound of formula 682 which is in the form of a methanol solvate

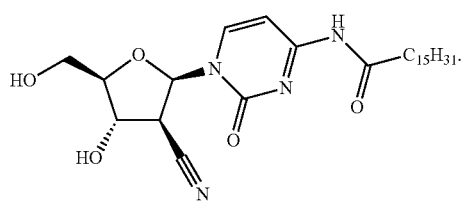

682

14. A compound according to claim 13 which is in crystalline form.

15. A process for preparing a compound of formula 682, said process comprising the steps of:

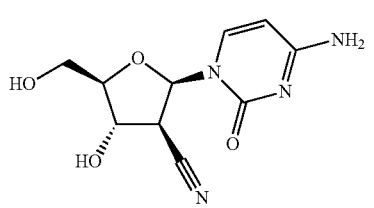

682-9

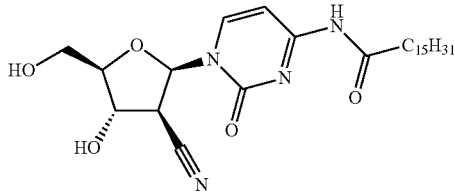

682

(i) treating a compound of formula 682-9 with palmitic anhydride in a mixture of H₂O/dioxane to form a compound of formula 682;

(ii) treating the product formed in step (i) with methanol to form a methanol solvate of the compound of formula 682 (form K);

(iii) isolating the methanol solvate of the compound of formula 682 (form K) formed in step (ii);

(iv) optionally purifying the product of step (iii) by recrystallization.

16. A process according to claim 15 which further comprises the steps of:

(a) converting the compound of formula 682 (form K) to a hemihydrate of the compound of formula 682 (form B) by a suspension form change reaction wherein the compound of formula 682 (form K) is suspended in methyl acetate containing approximately 1.5 to 2% low pyrogen water; and (b) optionally purifying the product formed in step (a) by crystallization.

17. A process according to claim 1, wherein the oxidizing reagent is 2,2,6,6-tetramethyl piperidinyloxy free radical (TEMPO) and NaOCl.

* * * * *

UNITED STATES PATENT AND TRADEMARK OFFICE
CERTIFICATE OF CORRECTION

| | | |
|---|---|---|
| PATENT NO. | : 8,884,001 B2 | Page 1 of 1 |
| APPLICATION NO. | : 12/991582 | |
| DATED | : November 11, 2014 | |
| INVENTOR(S) | : Gavin Wood et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 584 days.

In the Claims:

At column 24, line 67, in claim 2, insert -- of -- between "presence" and "$NEt_3$"

At column 25, line 9, in claim 2, delete "682-97" and replace with -- 682-9 --

At column 28, line 60, in claim 10, delete "$OfNEt_3$" and replace with -- of $NEt_3$ --

Signed and Sealed this
Fifteenth Day of September, 2015

Michelle K. Lee
*Director of the United States Patent and Trademark Office*